United States Patent [19]
Thorne et al.

[11] Patent Number: 5,848,692
[45] Date of Patent: Dec. 15, 1998

[54] UNIMOLD CONTAINER FOR DISCARDING MEDICAL MATERIAL

[75] Inventors: Gale H. Thorne; Gale H. Thorne, Jr., both of Bountiful; Charles V. Owen, Highland, all of Utah

[73] Assignee: Specialized Health Products, Inc., Bountiful, Utah

[21] Appl. No.: 878,043

[22] Filed: Jun. 18, 1997

[51] Int. Cl.$^6$ ..................................................... B65D 83/10
[52] U.S. Cl. ........................ 206/366; 206/63.5; 220/339; 220/908
[58] Field of Search ................................... 206/63.5, 366, 206/365, 438; 220/908–910, 337–339; 232/44, 47, 62

[56] References Cited

U.S. PATENT DOCUMENTS

| | | |
|---|---|---|
| 930,113 | 8/1909 | Adams . |
| 1,045,607 | 11/1912 | Payne . |
| 1,121,426 | 12/1914 | Walter . |
| 1,580,104 | 4/1926 | Hasselmann . |
| 1,697,359 | 1/1929 | Huffman . |
| 1,820,804 | 8/1931 | Huffman . |
| 2,226,215 | 12/1940 | Borah . |
| 2,338,315 | 1/1944 | Borah . |
| 2,435,994 | 2/1948 | Zukerman . |
| 2,962,155 | 11/1960 | Rusciano . |
| 2,971,688 | 2/1961 | Akers . |
| 2,990,059 | 6/1961 | Hitt . |
| 3,080,087 | 3/1963 | Cloyd . |
| 3,148,822 | 9/1964 | Yochum, Jr. . |
| 3,494,536 | 2/1970 | Henry . |
| 3,900,550 | 8/1975 | Oliver et al. . |
| 3,979,016 | 9/1976 | Frater . |
| 4,009,818 | 3/1977 | Rogers . |
| 4,037,754 | 7/1977 | Wilhelmi et al. . |
| 4,040,419 | 8/1977 | Goldman . |
| 4,106,621 | 8/1978 | Sorenson . |
| 4,121,755 | 10/1978 | Meseke et al. . |
| 4,149,578 | 4/1979 | Hickley . |
| 4,212,415 | 7/1980 | Neely . |
| 4,270,536 | 6/1981 | Lemelson . |
| 4,273,123 | 6/1981 | Lemelson . |
| 4,315,592 | 2/1982 | Smith . |
| 4,328,904 | 5/1982 | Iverson . |
| 4,375,849 | 3/1983 | Hanifl . |
| 4,452,358 | 6/1984 | Simpson . |
| 4,520,926 | 6/1985 | Nelson . |
| 4,576,281 | 3/1986 | Kirksey . |
| 4,600,112 | 7/1986 | Shillington et al. . |
| 4,679,700 | 7/1987 | Tharrington et al. . |
| 4,722,472 | 2/1988 | Bruno . |
| 4,733,778 | 3/1988 | Boeckmann et al. . |
| 4,779,728 | 10/1988 | Hanifl et al. ............................ 206/63.5 |
| 4,804,090 | 2/1989 | Schuh et al. . |
| 4,809,850 | 3/1989 | Laible et al. . |
| 4,816,307 | 3/1989 | Honeycutt . |
| 4,826,073 | 5/1989 | Bruno . |
| 4,840,272 | 6/1989 | Goldman . |

(List continued on next page.)

FOREIGN PATENT DOCUMENTS

| | | |
|---|---|---|
| 484294 | 5/1992 | European Pat. Off. . |
| WO 89/01905 | 3/1989 | WIPO . |

OTHER PUBLICATIONS

Devon Industries Product Brochure, Published 1993.

*Primary Examiner*—Paul T. Sewell
*Assistant Examiner*—Luan K. Bui
*Attorney, Agent, or Firm*—Gale H. Thorne

[57] ABSTRACT

A unimold sharps container and a unimold wall mount for a sharps container providing a sharps container system made from only two mold cavities. The sharps container is formed from a single mold cavity and comprises a well having four closed sides and a closed bottom and a top which is hingeably affixed to the well such that the entire container is assembled by folding interlocking parts of the container together. In similar fashion, the wall mount is made from a single mold cavity and comprises a secure attachment for a sharps container, yet a quick release feature which permits the container to be quickly and facilely remove for use away from the wall mount.

8 Claims, 12 Drawing Sheets

U.S. PATENT DOCUMENTS

| | | |
|---|---|---|
| 4,848,569 | 7/1989 | Leishman . |
| 4,874,103 | 10/1989 | Quisenberry et al. . |
| 4,890,733 | 1/1990 | Anderson . |
| 4,900,500 | 2/1990 | Honeycutt . |
| 4,903,832 | 2/1990 | Stewart . |
| 4,930,631 | 6/1990 | Bruno . |
| 4,936,449 | 6/1990 | Conrad et al. . |
| 4,946,064 | 8/1990 | VanCucha . |
| 4,969,554 | 11/1990 | Sawaya . |
| 4,979,616 | 12/1990 | Clanton . |
| 4,982,843 | 1/1991 | Jones . |
| 5,054,618 | 10/1991 | Kim . |
| 5,076,429 | 12/1991 | Patrick et al. ............ 206/366 |
| 5,080,251 | 1/1992 | Noack . |
| 5,103,997 | 4/1992 | Shillington et al. . |
| 5,117,997 | 6/1992 | Fink . |
| 5,176,256 | 1/1993 | Sawaya . |
| 5,183,180 | 2/1993 | Hawkins . |
| 5,184,720 | 2/1993 | Packer et al. . |
| 5,193,740 | 3/1993 | Newborough et al. . |
| 5,240,108 | 8/1993 | Tonna ..................... 206/366 |
| 5,251,779 | 10/1993 | Schmidt .................. 220/908 |
| 5,269,457 | 12/1993 | de la Fuente . |
| 5,271,500 | 12/1993 | Szacon . |
| 5,387,735 | 2/1995 | Ponsi et al. ............. 206/366 |
| 5,394,982 | 3/1995 | Sawaya . |
| 5,395,008 | 3/1995 | Bemis et al. ............ 206/366 |
| 5,419,435 | 5/1995 | Perzan et al. ........... 206/366 |
| 5,474,180 | 12/1995 | Robinson . |
| 5,570,783 | 11/1996 | Thorne . |
| 5,630,506 | 5/1997 | Thorne . |

Figure 15

UNIMOLD CONTAINER FOR DISCARDING MEDICAL MATERIAL

BACKGROUND OF THE INVENTION

1. Field of the Invention

The present invention relates generally to container assemblies which are useful for disposal of sharp medical instruments and other medical materials and more specifically to container assemblies and container wall mounts, each of which are made of a single molded part, commonly referred to herein as a unimold part.

2. The Present State of the Art

The possibility of exposure to AIDS or other life-threatening diseases by medical personnel in the process of disposing of used sharp medical instruments (sharps) has created an ever more present need for containers specially designed and used for safe disposal of sharps. For reference, the term "sharps" refers to sharp medical instruments such as syringes, scalpels, lancets, and the like, all of which require care and safe handling, especially when discarding a used and contaminated sharp. However, as important as providing safe means for disposing of contaminated sharps has become, criteria for selection of sharps containers for purchase are commonly based as much upon container price (user cost) as upon functionality and safety of the container.

There are many varieties of sharps containers and container systems commercially available for use in hospitals and alternate care environments. An example of a container system which can be used as a wall mounted sharps receptacle is disclosed in a reissued U.S. Pat. No. Re. 33,413, which is a reissue of U.S. Pat. No. 4,715,498 issued Dec. 29, 1987 to Paul H. Hanifl, (Hanifl '413 and Hanifl '498, respectively). Hanifl '498 and a U.S. Pat. No. 4,779,728 issued Oct. 25, 1988 to Paul H. Hanifl (Hanifl '728) disclose disposable containers for use in sharps container wall mount systems. Generally, such sharps containers severely restrict access to container interiors to lower likelihood of a user being injured by a previously thrown-away contaminated sharp.

It is common for disposable sharps containers to require molding and assembly of three to four injection molded parts for each such container. As an example, Hanifl '413 is seen to require at least three separately molded parts. The container disclosed in Hanifl '728 appears to require four separately molded parts.

A container requiring but two injection molded parts is disclosed in U.S. Pat. No. 5,630,506 issued May 20, 1997 to Thorne et al. (Thorne '506). The two parts comprise a well which has four solid walls integrally adjoining a solid bottom and a unimold top comprising an entry slot guarded by a biased flap and a cover which is opened to permit access to the entry slot and by which the biased flap is hingeably depressed to permit sharps to be discarded into the well.

Construction of each of the above mentioned containers requires coordination of molding machines and processes and after-molding activities to collect parts for assembly of each container. Of course, cost of such collecting and assembling must be passed along to a purchaser as part of overall cost of container manufacture.

Also, wall mounts for sharps containers are generally made from a plurality of parts. Just as with disposable containers, cost of wall mounts is also of concern in a commercial environment.

SUMMARY OF INVENTION

The present invention seeks to resolve a number of the problems which have been experienced in prior art, of which the above identified art are examples. More specifically, apparatus and methods within the scope of this invention constitute an important advance in the art of sharps container construction, as evidenced by the following objects and advantages realized by the invention over the prior art.

A primary object of the present invention is to provide a unimold container for disposal of sharps formed to include a well having four closed sides integral with a closed solid bottom and securely affixed to a top which provides a convoluted and tortuous discard path through an opening which makes hand insertion into the container difficult, if not impossible.

Another object is to provide a unimold container which, once removed from a mold, is assembled by a folding process.

Another object is to provide a top assembly for a unimold container which restricts inadvertent spillage of sharps from the container when the container is inverted.

An important object is to provide a biased flap closure over the opening in the top.

Another important object is to provide a permanent closure which securely restricts access to the container after the filling and closing of the container.

Additional objects and advantages of the invention will be apparent from the description which follows, or may be learned by the practice of the invention.

Briefly summarized, the foregoing objects are achieved by a container assembly which is formed in a single cavity mold. The assembly comprises a well having four closed sides integral with a closed solid bottom, two of the sides being hingeably affixed to two winged parts which, in combination, form a top for the container and an opening through which items are discarded into the container. The top comprises an opening-covering flap which is below, but biased upward toward the top to restrict entry into the well. The flap comprises a hinge attachment to one of the winged parts.

In a preferred embodiment, an entry shield which further restricts entry into the container is integral with the flap and is raised above the opening such that depression of the shield causes the flap to reflex against the bias and provide a more open entry into the well. Also in the preferred embodiment, inverted standoffs or spacers are provided which bias the flap at an angle which causes items deposited upon the flap to move toward the free end of the flap. It is also preferred that, when materials and molding processes permit, the flap be feathered to permit items to fall into the well without depression of the shield.

Each of the two winged parts comprise attachments which are complementary with attachment receivers, e.g. interlocking tabs and slots, respectively, which securely affix the winged parts to the well when the winged parts are folded to cover the well. When in the folded and secured state, the flap and shield cooperate to form a convoluted and tortuous discard path through the opening to restrict, as an example, hand insertion into the well.

It is a further object to provide a wall mount for a sharps container which is made from a single molded part.

These and other features of the present invention can be best understood from the following specification and drawings, of which the following is a brief description.

BRIEF DESCRIPTION OF DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention will be described with additional detail through use of the accompanying drawings in which.

DETAILED DESCRIPTION OF THE PREFERRED EMBODIMENT

Figure 1:
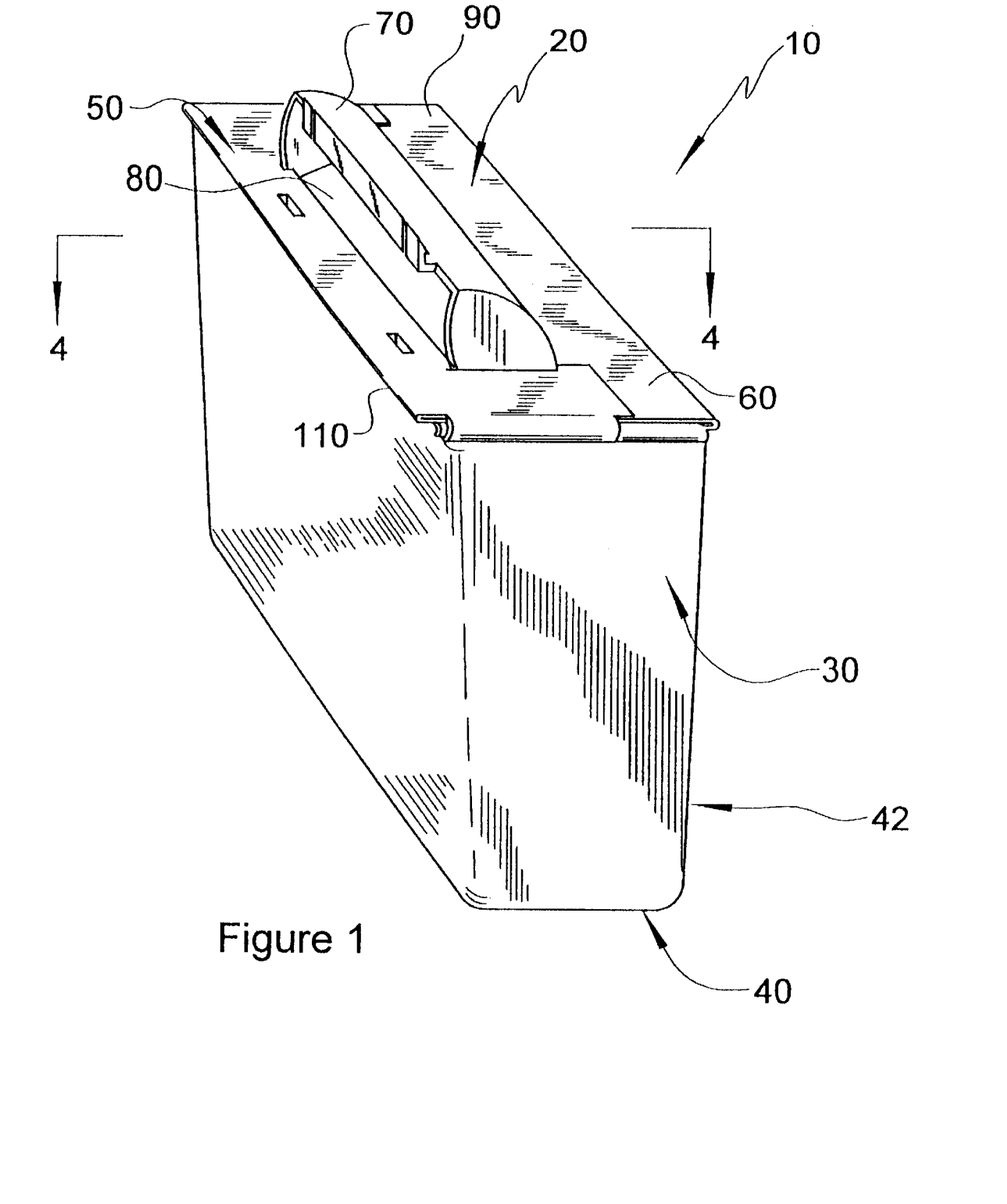
FIG. 1 is a perspective showing an assembled container.

Reference is now made to FIGS. 1–15 the drawings, wherein like numerals are used to denote like elements throughout. Primes are added to numbers to denote similar but not like elements. As seen in FIG. 1, an assembled container 10 comprises a superiorly disposed top 20 and four contiguous sides (generally numbered 30) and a bottom part 40 forming a well 42. Top 20 comprises a first (superiorly disposed) top part 50 and a second top part 60 (which is disposed inferiorly relative to part 50), both parts 50 and 60 being hingeably affixed to the rest of container 10. Container 10 may be made from any material into which may be molded living and biased hinges and which provides adequate puncture resistance to meet standards of performance for sharps containers. The presently preferred material is polypropylene.

As seen in FIG. 1, inferiorly disposed top part 60 comprises a shield 70, a biased flap 80 and a support rail 90. Portions of top part 60 and hidden sections of part 50 are better seen in FIG. 2.

Figure 2:
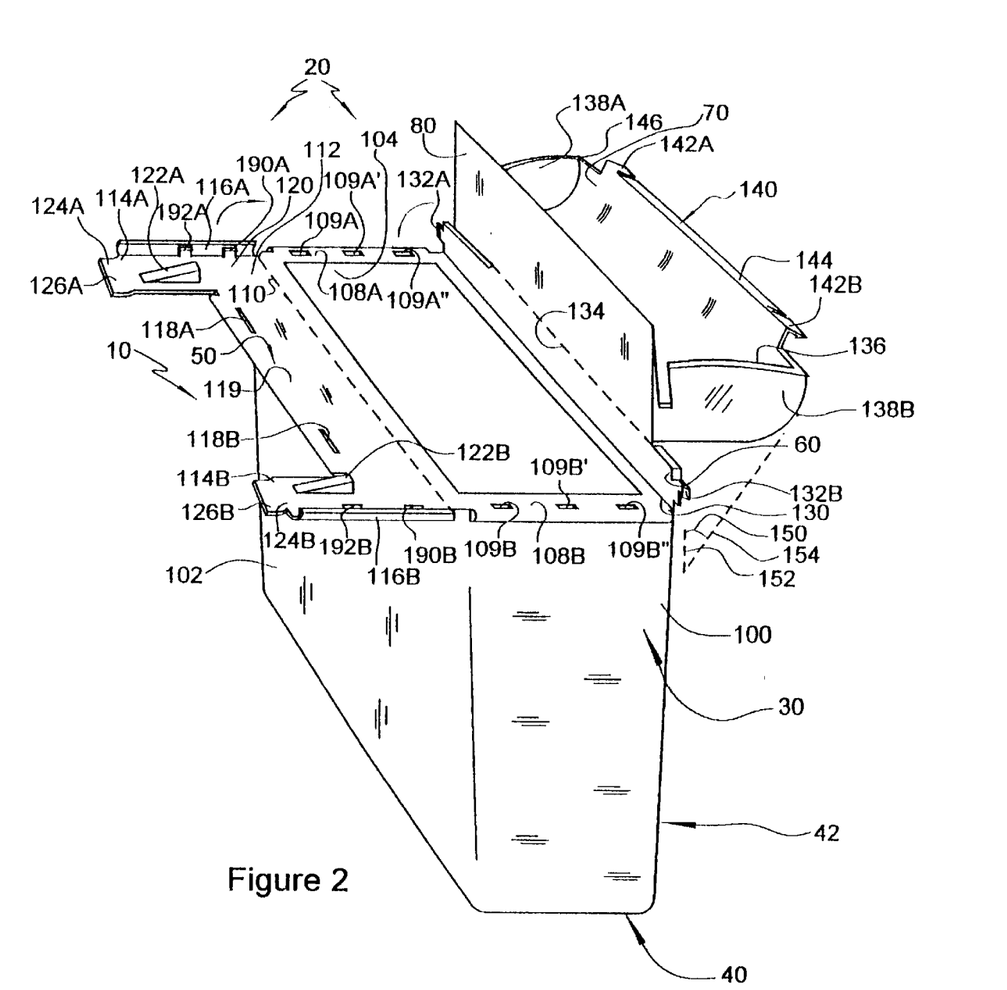
FIG. 2 is a container perspective portraying an as molded configuration.

Reference is now made to FIG. 2 wherein container 10 is seen in one as-molded or unassembled embodiment. In FIG. 2, portions of each of the four contiguous sides 30 (i.e. sides 100, 102, 104 and 106) are seen. In particular, narrower sides 100 and 104 comprise curved rim-forming top edges 108A and 108B, respectively. Curved edge 108A comprises three elongated slots 109A, 109A' and 109A". Likewise edge 108B comprises three elongated slots 109B, 109B' and 109B". The function of each of slots 109A, 109A', 109A", 109B, 109B' and 109B" is disclosed in detail hereafter.

Hingeably affixed to side 102, along dashed line 110, is part 50. Part 50 comprises a generally horizontal cross member 112, a pair of lateral extensions, numbered 114A and 114B, and two edge attachment segments, delineated by 116A and 116B.

Part 50 is generally elongated along hinge line 110 and comprises a pair of elongated slots 118A and 118B in a front plate portion 119. On one end 120, member 112 extends distally from hinge line 110 to form extension 114A. Extension 114A comprises a superiorly disposed wedge 122A. There purpose and geometric form of wedge 122A is disclosed in greater detail hereafter. More distal from line 110 than wedge 122A, extension 114A bends inferiorly at curvature 124A to form a lip 126A, the purpose for which is disclosed hereafter. In similar manner, but in mirror image perspective relative to extension 114A, extension 114B comprises wedge 122B, curvature 124B and lip 126B.

In the mold configuration seen in FIG. 2, support rail 90 is hingeably affixed to side 106 along a living hinge line 130 and molded essentially vertically upward from side 106. Rail 90 comprises two locking tabs 132A and 132B which are also molded with hinge attachments to the rest of rail 90. Superiorly disposed through a biased flap hinged along line 134, biased flap 80 and shield 70 are joined to rail 90. As seen in FIG. 2, biased flap 80 is thinned as it extends away from line 134. Such thinning serves two purposes, forming a draft which facilitates release from a mold and making biased flap 80 less resilient as it extends away from hinge line 134. The reason for having such less resiliency is described hereafter.

As disclosed above, integral attachment of shield 70 is made superior to hinge line 134. Shield 70 comprises a somewhat cylindrical, curved shell 136 which is mostly closed at its ends, 138A and 138B. Disposed at an open face 140 of shield 70 are a pair of locking tabs 142A and 142B and an elongated bar 144. When shield 70 is disposed in an as used state, as seen in FIG. 1, a transverse tangent line off leading edge 146 of shield 70 is substantially parallel with rail 90. However, biased flap 80 is tilted at an angle toward front plate portion 119, being biased at an angle at which friction is substantially overcome causing items disposed upon flap 80 to slide or roll under plate portion 119. Locking tabs 142A and 142B each comprise a living hinge attachment to leading edge 146 permitting an approximate 180° rotation for use in permanent closure of container 10.

As denoted by angle 150, formed by intersection of vertical line 152 and line 154 which is tangent to leading edge 146, shield 70 opens at an obtuse angle relative to the vertical plane of biased flap 80, permitting ready release of shield 70 from a mold. In the mold configuration of FIG. 2, container 10 is moldable without side pulls. It may be noted that angle 150 is the same angle that biased flap 80 is biased by interaction with wedges 122A and 122B when folded and assembled as seen in FIG. 1.

Figure 3:
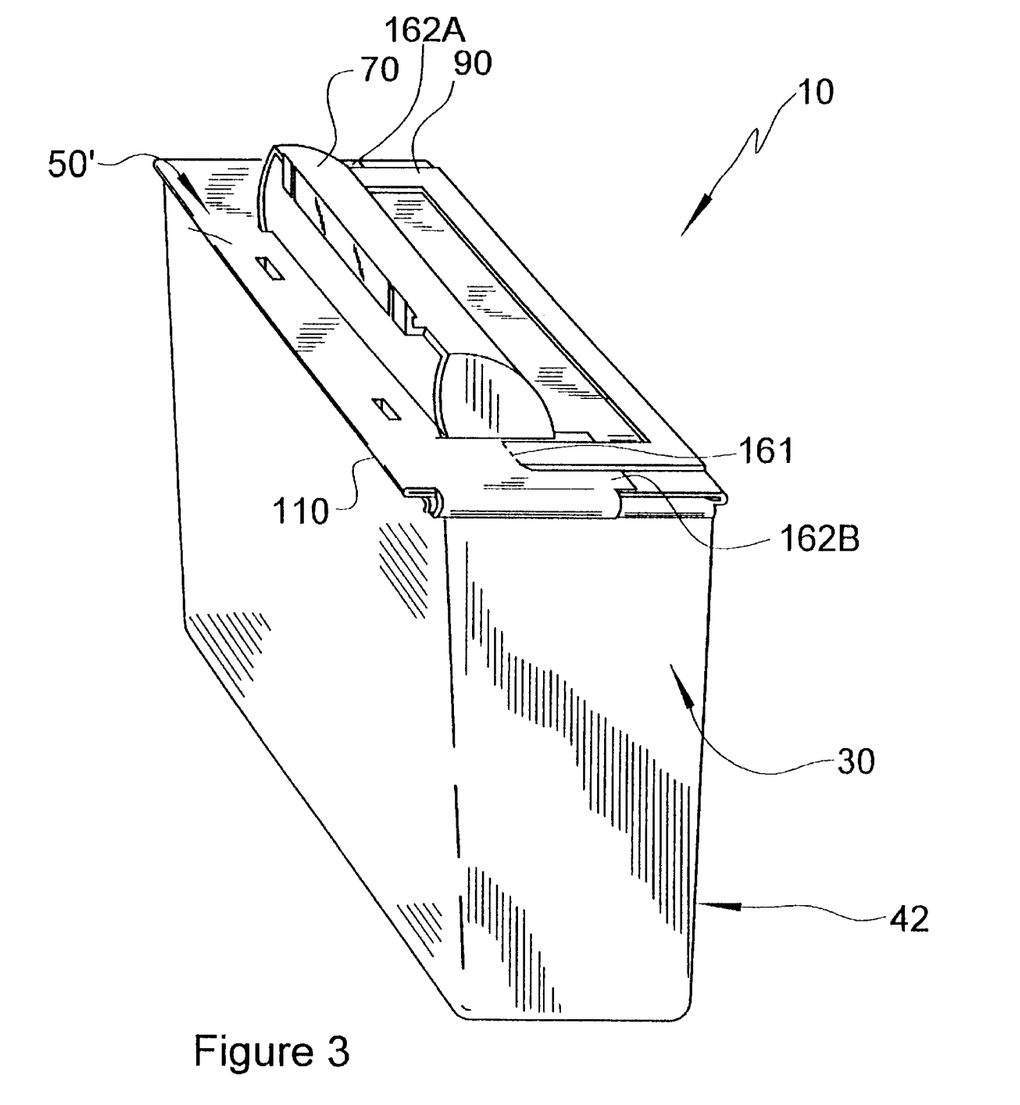
FIG. 3 is a perspective of a container which is similar to the container seen if FIG. 1 but having a handle integrally molded as part of the container top.

Reference is now made to a container 10', seen in FIG. 3. Container 10' comprises a plurality of parts which are like those of container 10 with exception of part 50. Container 10' comprises a part 50' which has an added handle element 160 which differentiates part 50' from part 50. Note that handle element 160 is connected to the rest of part 50' through a living hinge, depicted on one side of container 10' by a line 161. Such disposition of the hinge at line 161 permits the container to be lifted nearly in line with the container's center of gravity.

In container 10', wedges 122A and 122B are each disposed below a separated portion 162A and 162B, respectively, of part 50'. Also, each portion 162A and 162B may comprise an interlocking tab or plug (not shown) when necessary to preserve mechanical integrity due to opposing forces between biased flap 80 and wedges 122A and 122B.

Figure 4:
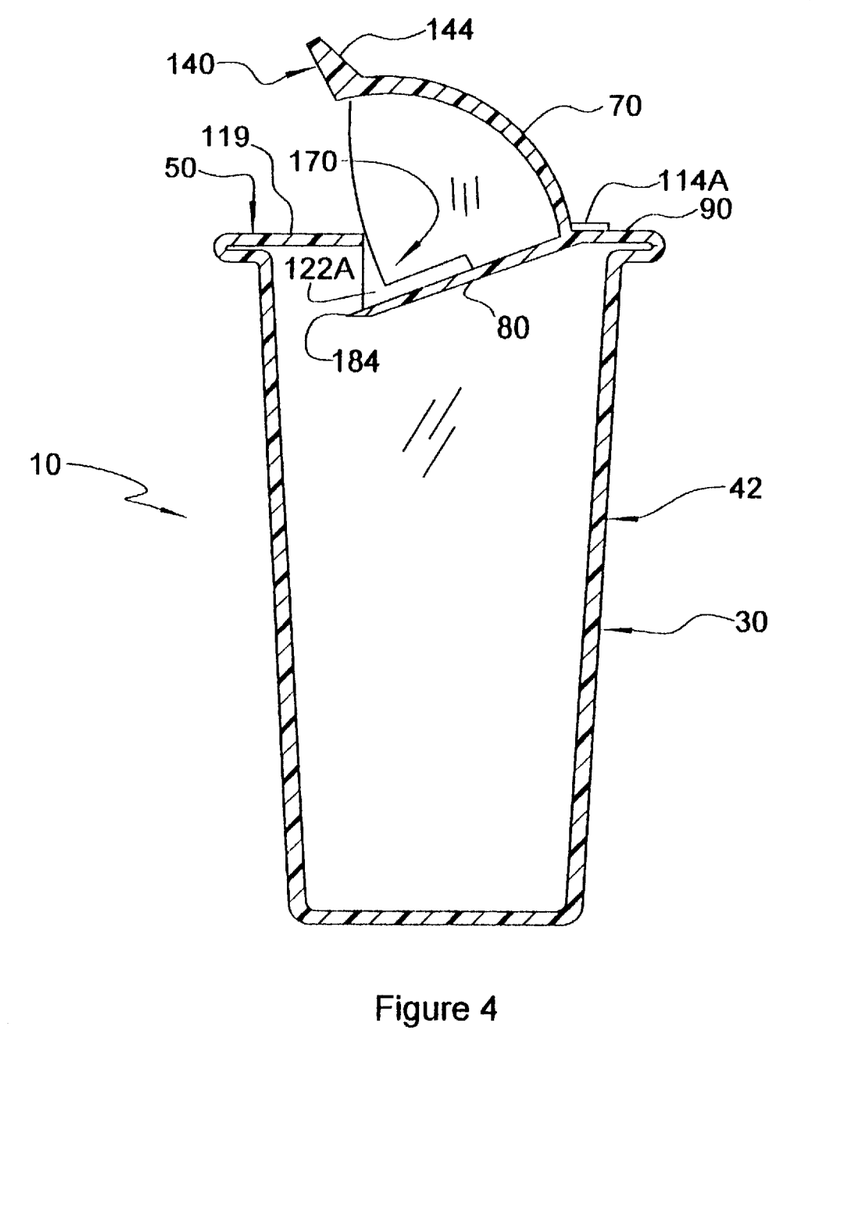
FIG. 4 is a cross-sectional view taken along lines 4—4 of FIG. 1 and showing biased flap and shield disposed in a rest state.
Figure 5:
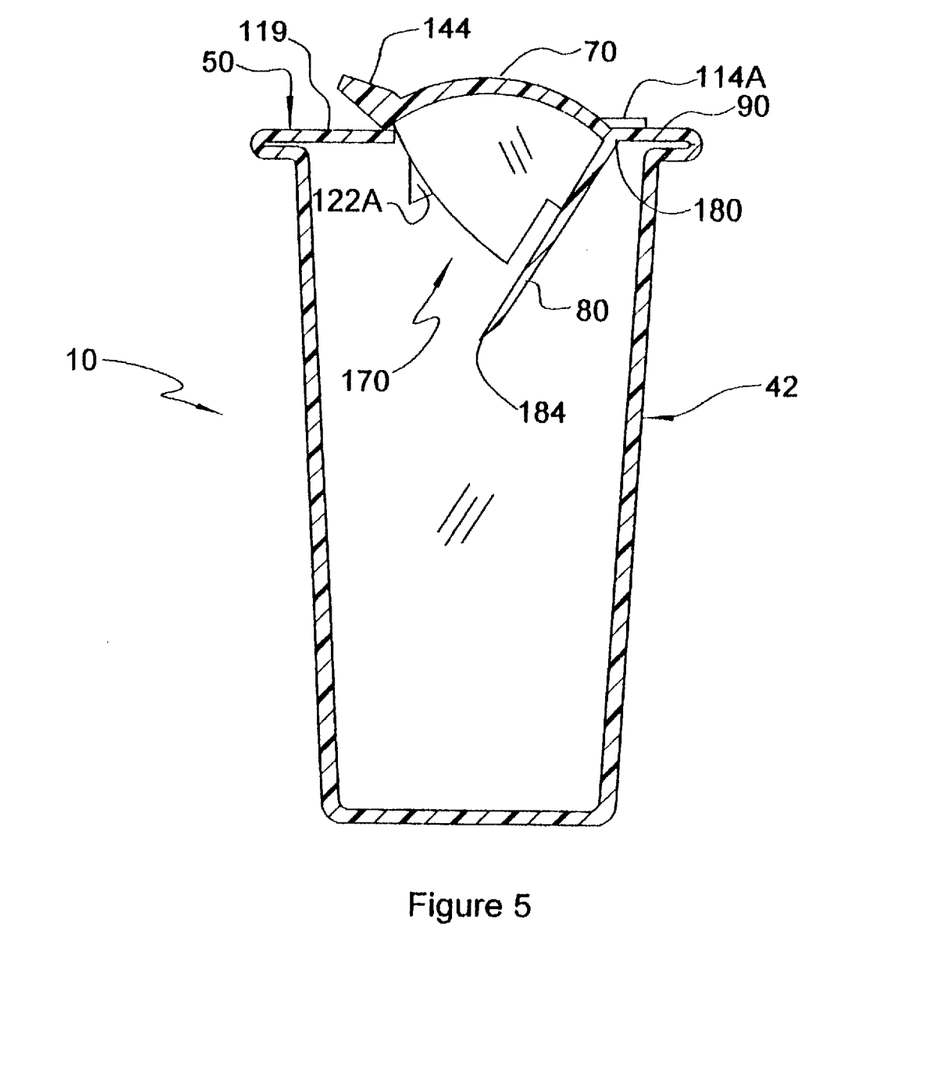
FIG. 5 is a cross-sectional view similar to the view of FIG. 4, but showing shield depressed to deflect the biased flap for open entry into the well of the container.

Reference is now made to a cross section of container 10 seen in FIG. 4 wherein angulation of biased flap 80 in cooperation with angulation of wedge 122A is demonstrated. Note that an opening 170 between plate portion 119 and biased flap 80 permits small items discarded upon biased flap 80 to slide or roll directly into well 42. However, larger items or parts which slide less freely may not move on their own into well 42.

It is for this reason that shield 70 is integrally attached to a hinge 180 and biased flap 80. Note, in FIG. 5, that rotation of shield 70 by pressing on a superior portion of shield 70, e.g. bar 144, similarly rotates biased flap 80 about hinge 180 to widen opening 170 significantly, permitting larger items to drop into well 42. Note, also, that closure of bar 144 and forward edge 140 against plate portion 119 restricts digitary access to well 42 as opening 170 is widened.

Figure 6:
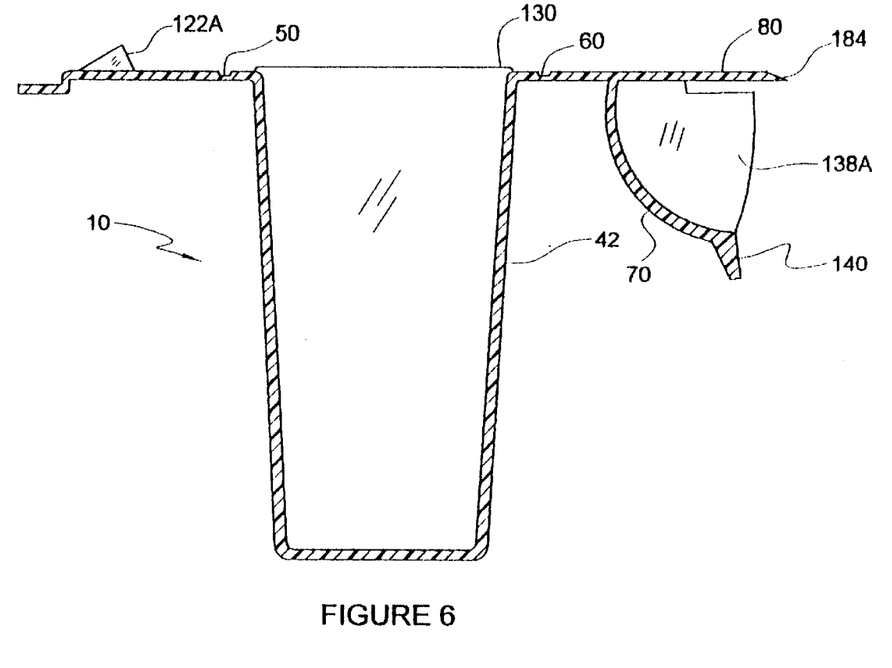
FIG. 6 is a cross section of a container similar to the container of FIG. 1, but molded in a different configuration than that seen in FIG. 3.
Figure 7:
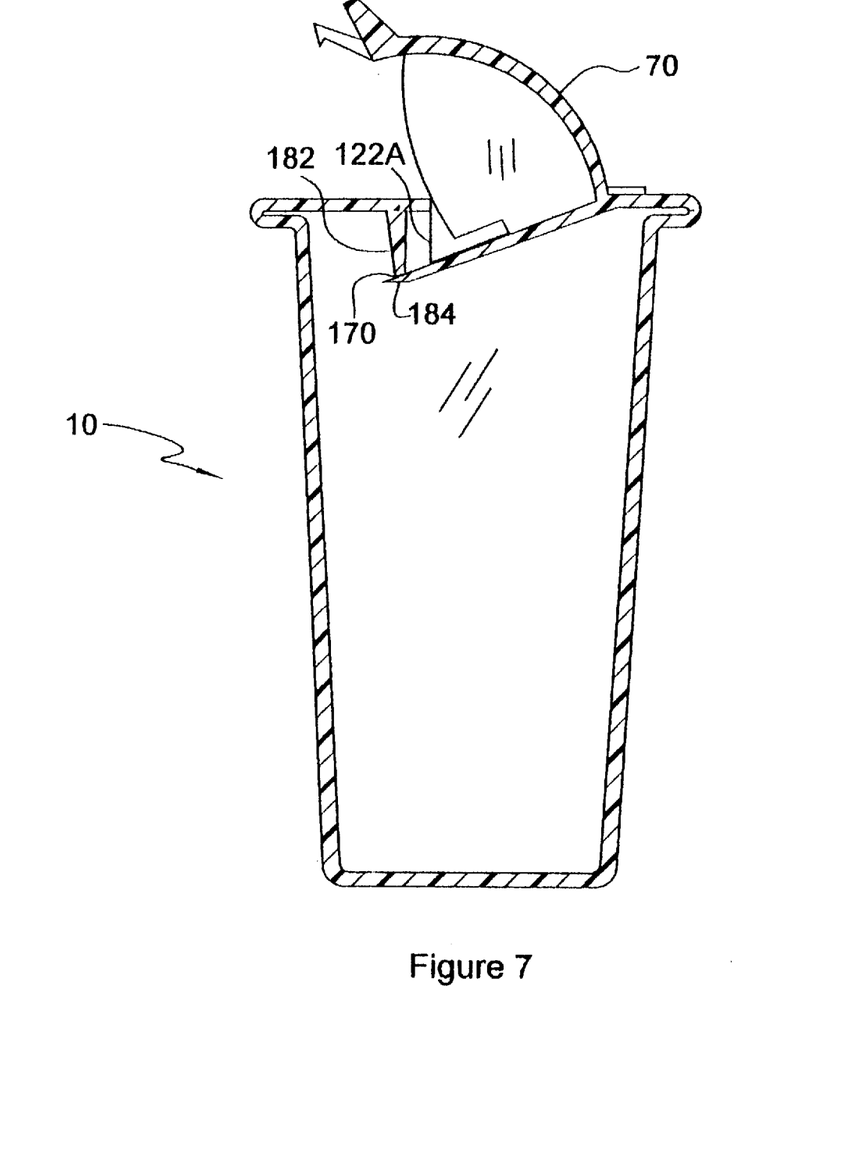
FIG. 7 is a cross section similar to the cross section of FIG. 4, but showing additional parts.

Reference is now made to FIG. 6, wherein another mold embodiment is seen in cross section. Note that the molded plane of top part 60 is horizontally disposed. This embodiment significantly reduces the height of a unimolded part and its associated mold. However, also note that a side pull is required in the formation of shield 70.

In some cases, further restriction of opening 170 may be desired. In such a case, addition of a distending bar 182 may be added to an inferior side 119 (superior side when disposed in an as molded state). Also, feathering of biased flap 80 toward its free edge 184 to a degree which permits bending of flap 80 upon added weight of an item disposed thereon, would further permit discarding of some parts into container 10 without depressing shield 70.

The embodiment seen in FIG. 6 is presently preferred because mold depth is reduced by horizontal disposition of top parts 50 and 60. This embodiment is further preferred because of added facility in keying and anchoring mold core to mold cavity. To maintain a consistent wall thickness of well 42 it is imperative to keep the mold core from shifting within the mold cavity due to inherent pressures required to cause plastic flow across living hinges and other area reduced openings. As one who is skilled in the art of mold design is aware, adequate keying and anchoring is a necessary part of quality mold construction.

A primary feature of these instant inventions is ease of fabrication. Each sharps container and wall mount, disclosed hereafter, is assembled by simply folding then snapping parts together. As an example, container 10 requires but two assembly steps. As best seen in FIGS. 2 and 6, once container 10 is removed from its mold, simply folding top part 60 over container well 42 along hinge line 130 permits tabs 132A and 132B to be snapped into slots 109A" and 109B" to securely affix rail 90 in place. Then top part 50 is likewise folded over well 42 and tabs 190A, 192A, 190B and 192B (as seen in FIG. 2) are snap-fitted into slots 109A, 109A', 109B and 109B', respectively. Affixing top part 50 above to top part 60 results in each wedge 222A and 222B communicating with biased flap 80 to cause flap 80 to slant downward toward its free edge 184. The downward slant is best angled to cause items disposed upon flap 80 to slide or roll toward edge 184. In some applications, it is preferred that no additional effort is required after discarding an item into a sharps container than the act of discarding itself. For this purpose, it may be preferred to "feather" biased flap 80 toward edge 184 such that, in the vicinity of edge 184, flap 80 can only support its own weight. Thus, a discarded item which rolls or slides toward edge 184 displaces flap 80 downwardly at edge 184 and falls unaided into well 42.

Figure 8:
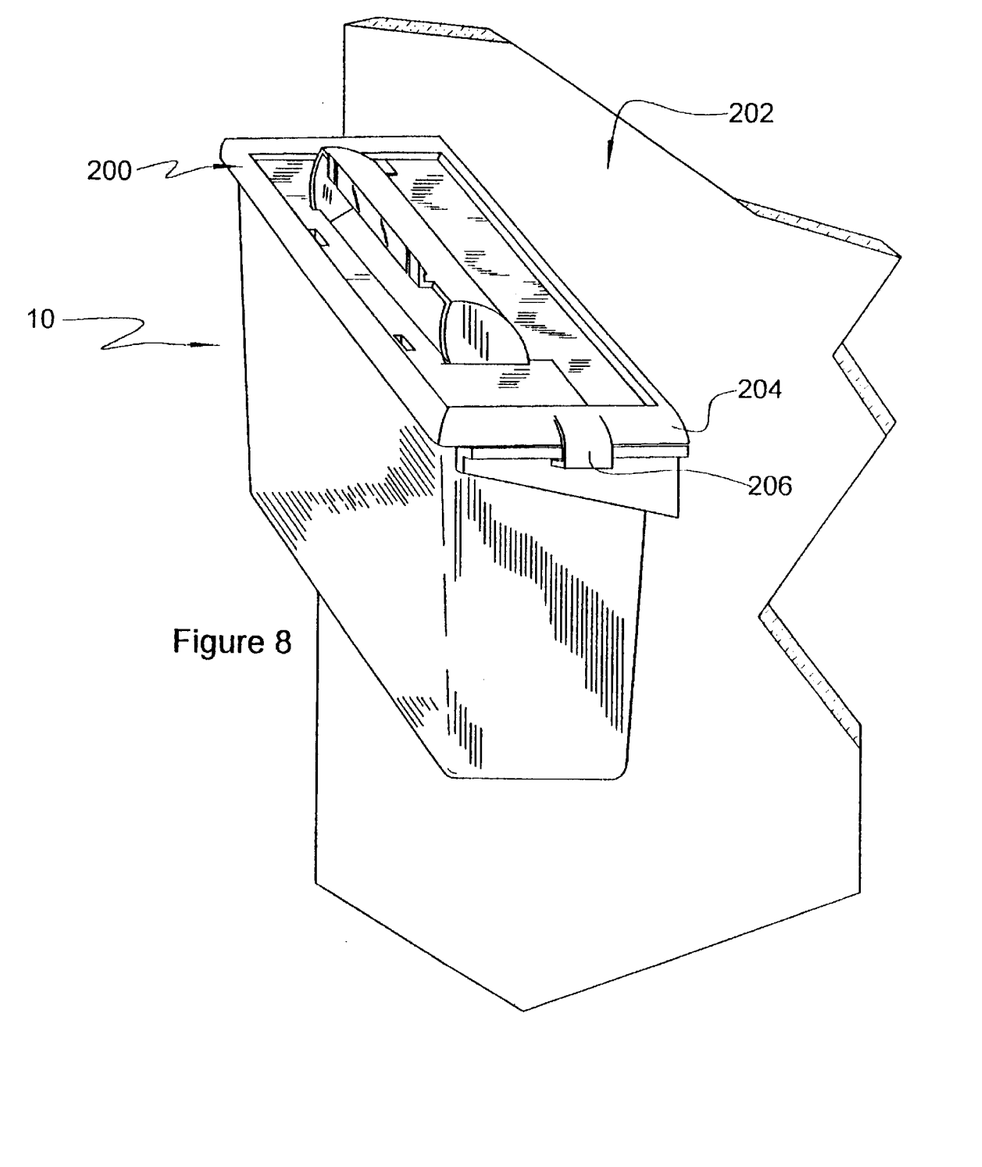
FIG. 8 is a perspective of the container of FIG. 1, affixed to a wall with a unimold wall mount.

Wall mounts for sharps containers are customarily provided in hospital rooms and other places where sharps containers are made readily available for safe disposal of sharps. Reference is now made to FIG. 8 where in a unimold wall mount 200 is seen supporting a sharps container 10 upon a wall 202. Wall mount 200 comprises a frame 204 upon which a latch release 206 is provided. Construction and details of wall mount 200 are better seen in FIGS. 9–12.

Figure 9:
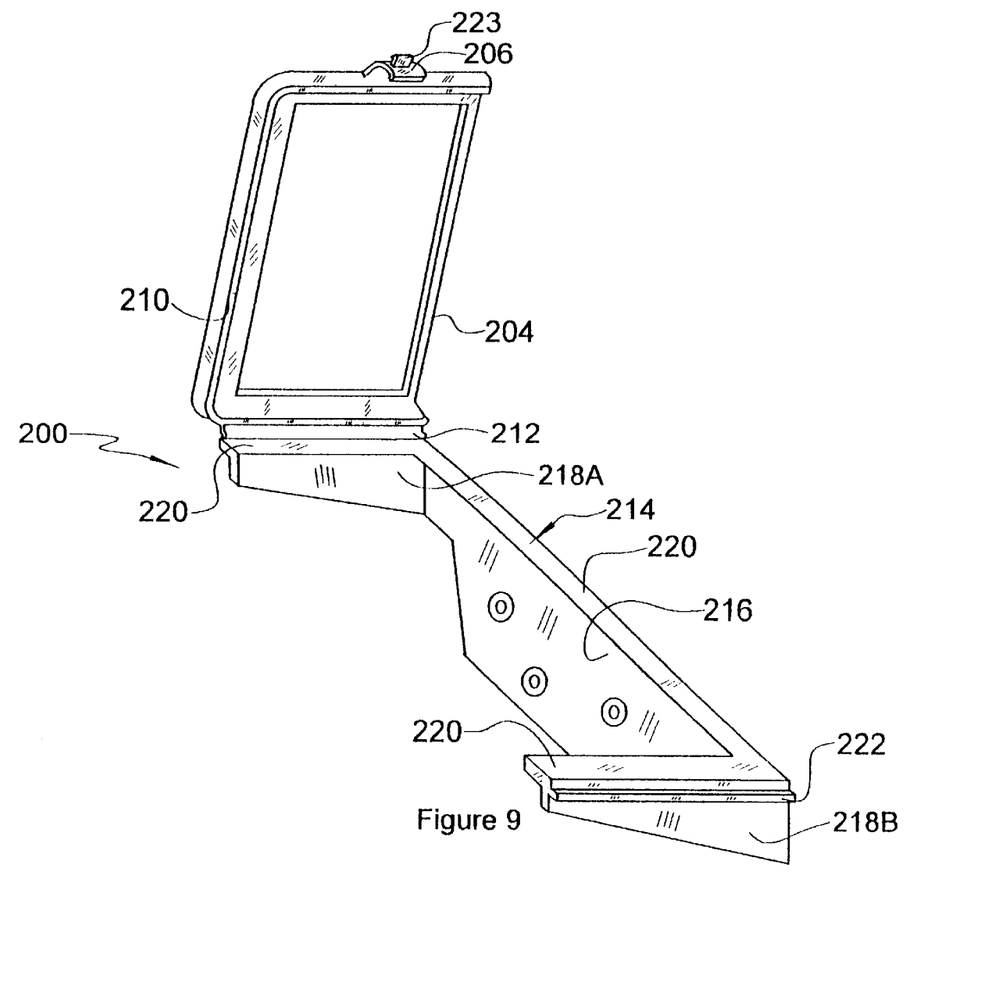
FIG. 9 is a perspective of the wall mount of FIG. 8, open and unloaded.

Wall mount 200 is seen disposed in a partially opened state with container 10 removed in FIG. 9. Frame 204 comprises a rim 210 which is downwardly distended when wall mount 200 is disposed to contain a sharps container. Hingeably connected via a living hinge 212 is a mounting shelf 214. Mounting shelf 214 supports the sharps container through a mounting support plate 216 by which shelf 214 is fastened to a wall, such as wall 202 of FIG. 8. Extending distally from the wall are two shelve supports 218A and 218B. A contiguous flat shelf plane 220 is provided for horizontal support of a rim around the outside of a sharps container, such as edges 108A and 108B or other available support edges or rims commonly found around peripheral attachments of tops to wells of other sharps containers.

Of course, as is common and well known in the manufacture of molded parts, mounting shelf 214 should be provided with appropriate structural ribs and other strengthening members to assure competent performance. In addition, shelf 218B comprises a horizontal rail 222 which acts as a releasible catch for latch and latch release 206. Latch and latch release 206 may be keyed for added security. Such keying is well known in the art of locks making. Latch release 206 may comprise a release handle 223 for ease of unlatching.

For use wall mount 200 is affixed to a vertical wall or other vertical surface. While wall mount 200 is open, a container, such as container 10, is disposed upon shelf 214. Frame 204 is hingeable lowered to latch 206 upon rail 222, firmly securing the container to wall mount and wall or other vertical surface. When it is desired to move or remove the container from the wall mount, latch 206 is (unlocked, if locked and) disengaged, frame 204 is hingeably raised and the container is slid off plane 220.

Figures 10, 11:
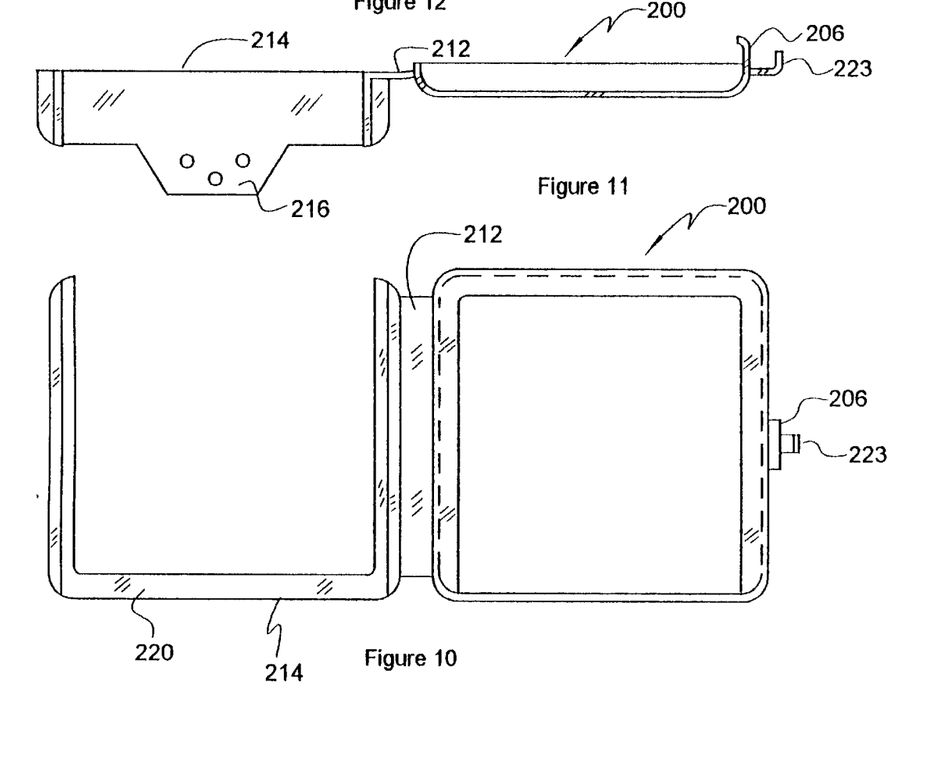
FIG. 10 is an as molded bottom elevation of the wall mount seen in FIGS. 8 and 9.
FIG. 11 is an as molded side elevation of the wall mount seen in FIGS. 8 and 9.
Figure 12:
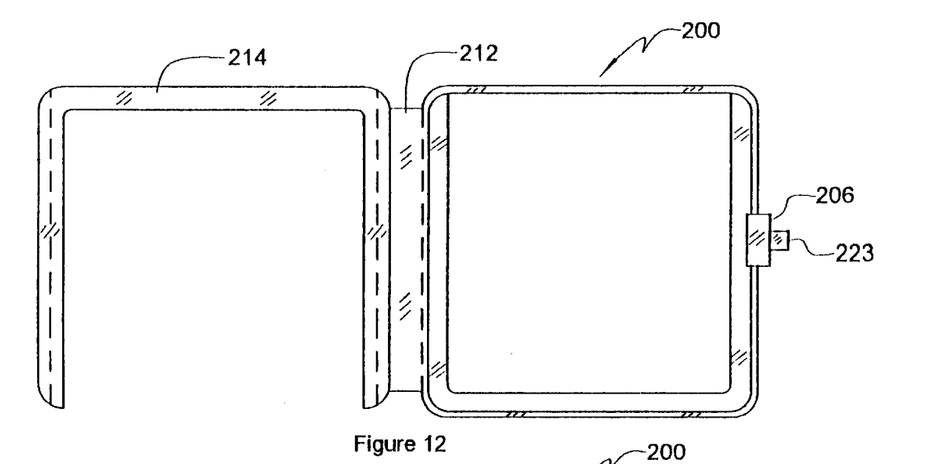
FIG. 12 is an as molded top elevation of the wall mount seen in FIGS. 8 and 9.

FIGS. 10–12 provide three elevational views of wall mount 200 as molded. Dashed lines are indicative of hidden edges.

Figure 13:
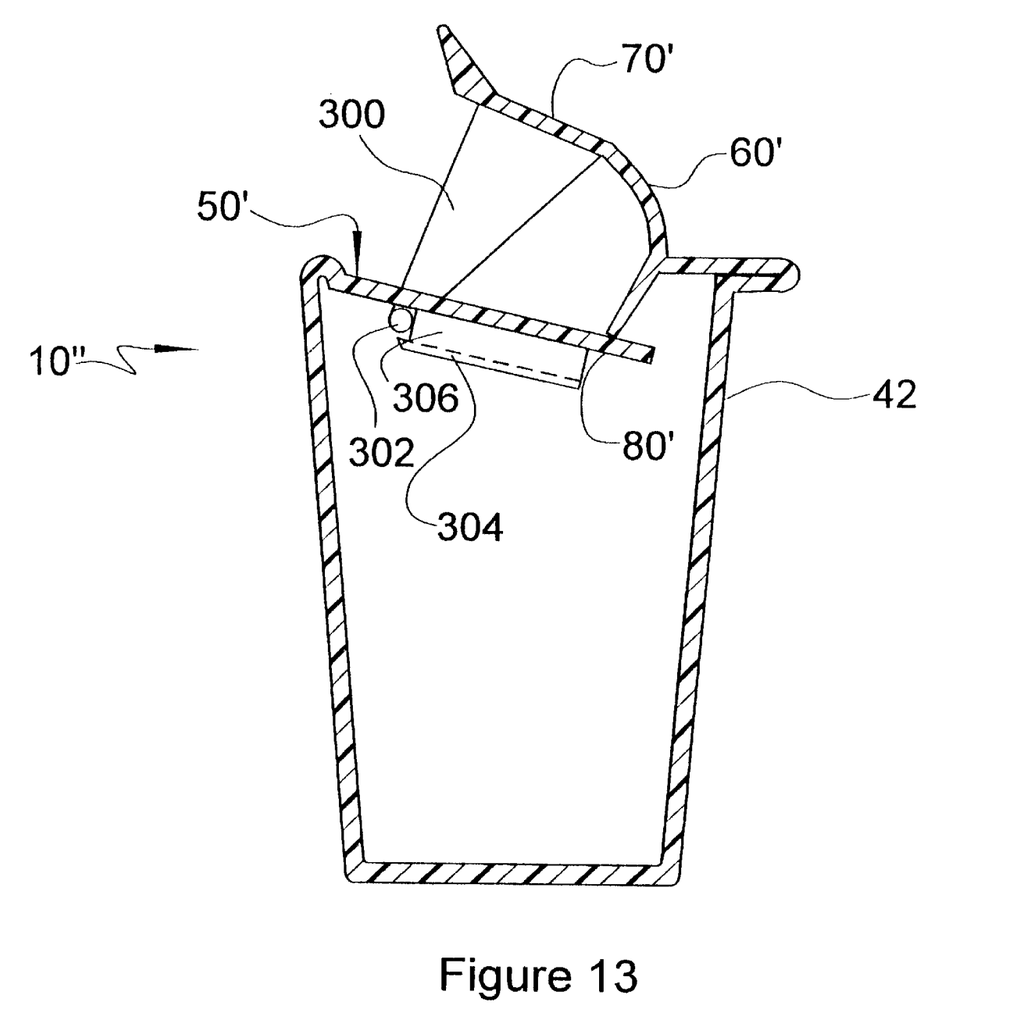
FIG. 13 is a cross section of a unimold container similar to the container seen in FIGS. 1–7, but having a biased flap and a shield disposed hingeably affixed to opposite sides of the container.
Figure 14:
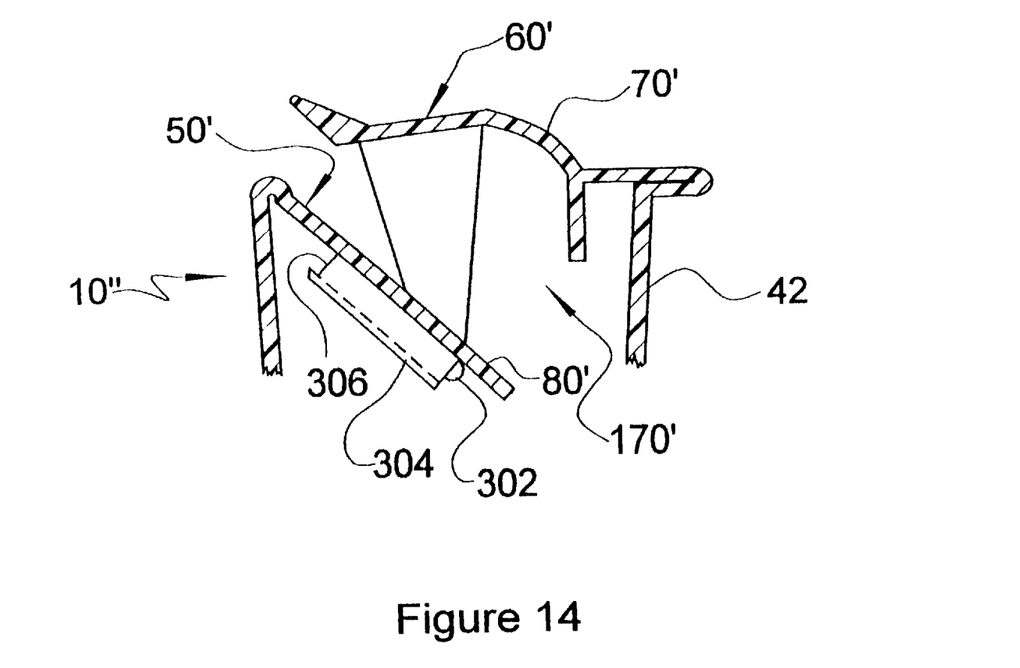
FIG. 14 is a segmented cross section of a portion of the container seen in FIG. 13 which both biased flap and shield depressed to provide access into the container well.
Figure 15:
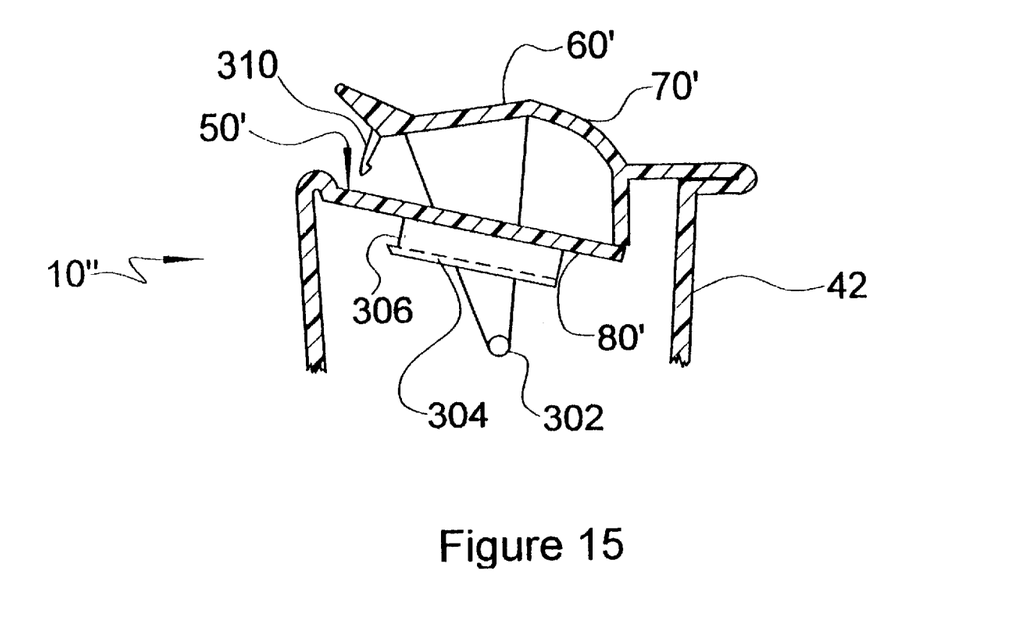
FIG. 15 is a segmented cross section of the portion of the container seen in FIG. 14 with the biased flap released to at least partially close access to the container well.

Reference is now made to FIGS. 13–15 wherein another embodiment of a unimold sharps container 10" is seen. While container 10" is only seen in cross section in FIGS. 13–15, it should be understood that the general appearance of container 10" is similar to the appearance of container 10.

As an example, container 10" comprises a well 42 which is substantially the same in form and function to well 42 of container 10. Similar to container 10, container 10" also comprises two hingeably affixed top parts 50' and 60'.

However, a biased flap 80' of container 10' is a section of top part 50'. And shield 70' is a segment of top part 60'.

Further shield 70' comprises a pair of arms, one of which is seen as arm 300, formed as a hinged section of shield. Arm 300 comprises a slider pin 302.

Biased flap 80' comprises a pair of structures, disposed in mirror image orientation, one of which is seen as structure 304 in FIGS. 13–15. Hidden edges and parts of structure 304 and arm 300 are shown by dashed lines. A detailed disclosure of a similar arm, slider pin and structure associated with opening a biased flap is disclosed in detail in Thorne '506.

In container 80', slider pin 302 is disposed to enter a slide path 306 of structure 304 when shield 70' and biased flap 80' are both superiorly oriented, as seen in FIG. 13. When shield 70' is depressed toward well 42, slider pin 302 moves along path 306 causing biased flap 80' to angularly rotate inferiorly into well 42 to clear an opening 170', as seen in FIG. 14. Release of shield 70' before slider pin 302 clears path 306 permits shield 70' and flap 80' to cooperatively close opening 170'. Further, depression of shield 70' causes slider pin 302 to proceed out of path 306 and structure 304 whereupon biased flap 80' is released to at least partially close opening 170'.

In this state, as seen in FIG. 15, shield 70' may be raised to the orientation seen in FIG. 13 or a tab 310, similar in form and function to tab 142A seen in FIG. 2, may be inserted through a slot (not shown) in flap 80' to permanently lock container 10" closed.

In summary, the method and apparatus disclosed herein represent a significant improvement from the present state of the containers and wall mounts, providing a unimold design and simple fold-to-assemble construction. The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A container assembly for disposing of medical shares which is formed as a singles integrally molded component, said container assembly comprising:

a waste containment well having four closed sides integral with a closed solid bottom and a superiorly disposed opening;

a top providing a cover over the opening of the container assembly well, said top comprising:

living hinge and locking tab connections whereby the top is foldably disposed and firmly fastened, respectively, to the well to securely cover the opening;

an aperture, disposed to be in line with the opening, through which items are discarded into said well;

a flap biased upwardly by and through an associated living hinge to cover said aperture in one state and displaced downwardly by a force applied externally against the upward bias to uncover the aperture and allow access to the well in another state; and a shield which is superiorly disposed relative to said biased flap and which communicates with said biased flap and associated hinge to provide an entry through the aperture and access to the well when the shield is downwardly disposed.

2. A container assembly for disposing of medical sharps according to claim 1 wherein said top comprises two parts, each part comprising a connection via a living hinge to a side of the container assembly opposite the living-hinge connection of the other part.

3. A container assembly for disposing of medical sharps which is formed as a single, integrally molded component, said container assembly comprising:

a waste containment well having four closed sides integral with a closed solid bottom and a superiorly disposed opening;

a top providing a cover over the opening of the container assembly well, said top comprising:

two parts cooperatively forming the top, each part comprising a connection via a living hinge to a side of the container assembly opposite the living-hinge connection of the other part, said top forming parts in combination comprising:

an aperture, disposed to be in line with the opening, through which items are discarded into said well;

a flap biased upwardly by and through a living hinge affixed to the frame to cover said aperture in one state and downwardly disposed by an externally applied force to uncover the aperture and allow access to the well in another state;

a shield which is superiorly disposed relative to said biased flap and which cooperates with said biased flap to provide an entry through the aperture and access to the well when the shield is downwardly disposed; and one of said hinged parts further comprising a wedge which causes the biased flap, in the one state, to be disposed at an angle relative to horizontal such that discarded items disposed upon the flap are prone to move under influence of gravity toward a free end of said flap.

4. A container for disposing of medical sharps which is suitable for being used in cooperation with a container wall mount and which is formed as a single, integrally molded component, said container comprising:

a container body comprising four closed sides integral with a closed bottom and a superiorly disposed opening;

a top, which selectively covers the opening, comprising:

a first top part comprising a lateral cross member, a pair of lateral extensions, a living hinge whereby the first top part is affixed to the container body and at least one tab for securing the first top part to the body;

a second top part, inferiorly disposed relative to the first top part, comprising a shield, a biased flap, a support rail, a living hinge whereby the second top part is affixed to the container body and at least one tab for securing the second top part to the body about the opening, said first top part and second top part, in combination, defining an aperture through which sharps and other waste products are passed through the top opening into the container body;

the flap being biased upwardly by and through a living hinge to restrictively contact the first top part to cover the aperture in a first state, the flap being dislocated from covering said aperture by an externally applied force to provide a pathway through the aperture in a second state;

the entry shield comprising attachment to the rest of the second top part by a living hinge, said shield communicating with said flap such that, when the shield is forced downward, the flap is displaced to the second state to permit access to the pathway and, when force upon the entry shield is removed, the flap is permitted to reflexively return to the first state.

5. A container for disposing of medical sharps according to claim 4 further comprising a handle by which the container is carried.

6. A container for disposing of medical sharps according to claim 1 wherein said entry shield comprises means for temporarily affixing the entry shield to said biased flap whereby said biased flap is opened as said entry shield is partially closed, but is released to reflex to the closed position when the entry shield is fully closed and which is temporarily reaffixed to the biased flap when the entry shield is opened.

7. A container for disposing of medical sharps according to claim 4 wherein said biased flap in cooperation with said entry shield comprise means for creating a tortuous path into the well to provide a safety barrier for protecting against contact with sharps disposed in the well.

8. (Twice Amended) A container for disposing of medical sharps according to claim 4 wherein said first top part comprises locking slots and said entry shield comprises locking tabs which in combination provide a means for permanently locking the entry shield to the first top part, thereby precluding any further discarding of waste products into the container.

* * * * *